United States Patent [19]

Ellis

[11] 4,189,936
[45] Feb. 26, 1980

[54] PRESSURE GENERATOR

[76] Inventor: David M. Ellis, 11 Fern Way, Bedford, Mass. 01730

[21] Appl. No.: 951,021

[22] Filed: Oct. 13, 1978

[51] Int. Cl.² .............................................. G01L 27/00
[52] U.S. Cl. ...................................................... 73/4 R
[58] Field of Search ................... 73/4 R; 417/412, 413

[56] References Cited
U.S. PATENT DOCUMENTS

| 2,669,937 | 2/1954 | Presently | 417/413 |
| 3,273,505 | 9/1966 | Miles | 417/413 |
| 3,868,844 | 3/1975 | Klein | 73/4 R |

Primary Examiner—S. Clement Swisher
Attorney, Agent, or Firm—Joseph S. Iandiorio

[57] ABSTRACT

A variable volume pressure wave generator including a drive magnet; a low mass, drive coil for energization by an electrical analog of a pressure wave to be simulated and driven by interaction with a magnet; a low mass, high compliance drive coil suspension for supporting the coil relative to the magnet; a piston interconnected and driven with the drive coil; a pressure chamber having an opening for receiving the piston; a flexible, inelastic, diaphragm sealingly engaged with the piston and with the chamber; and passage means extending from the chamber for external connection.

3 Claims, 11 Drawing Figures

NEUTRAL POSITION	DEFLECTED POSITION

PRESSURE GENERATOR

FIELD OF INVENTION

This invention relates to an improved pressure simulator and more particularly to an improved pressure generator for use in such a simulator.

BACKGROUND OF INVENTION

It is common medical practice to directly measure blood pressure of critically ill patients. In contrast to the intermittent measurement of systolic and diastolic blood pressures using an inflated cuff on the arm and a stethoscope, direct pressure measurement allows continuous unattended monitoring of the patient's status.

In brief, direct blood pressure measurement is done as follows: a small tube called a catheter is placed in an artery. Typically, this is the radial artery in the wrist. A length of extension tubing connects the catheter to a pressure transducer. The transducer dome, the extension tubing, and the catheter are filled with saline solution. Various valves, stopcocks, and flush devices allow for filling the tubing system with fluid, for flushing the catheter with fluid to prevent clotting of the catheter tip, and for the withdrawal of blood samples for diagnostic tests.

The pressure signal detected by the pressure transducer is amplified and displayed on a monitoring oscilloscope. This allows direct viewing of the pressure wave generated by the beating of the patient's heart. The amplified pressure signal is also sent to circuitry which extracts the highest and lowest pressures found in the wave. These are known, respectively, as the systolic and diastolic pressures, and are typically displayed on the blood pressure monitor. Therapy is guided by the measured systolic and diastolic pressures.

In order for the blood pressure monitor to function properly, the pressure measured at the transducer must be an accurate replica of the pressure in the patient's blood vessel at the tip of the catheter. If the blood pressure were constant, having no pulsatile component, only the difference in height, and the resulting hydrostatic head between the heart and the transducer would have to be taken into account. However, this is not the case and so with the pressure pulses found in both the systemic and pulmonary arteries, the dynamic properties of the fluid filled tubing and the associated valves and transducer must be carefully controlled to obtain accurate transmission of the pressure waves from the blood vessel to the pressure transducer.

There are two common situations which lead to clinically significant distortion of the pressure wave, and to incorrect systolic and diastolic values being measured. The first is the use of inappropriate tubing and/or valves. If the tubing is too long, too small in diameter, or too soft and compliant, wave form distortion results. The second is the presence of small air bubbles in the fluid filled system. The presence of bubbles, especially near or at the transducer, produces resonant behavior. For example, a bubble of 3 cubic millimeters volume near the transducer in a typical clinical setup may cause the systolic pressure to read 10 to 30 mmHg. higher at the transducer than in the catheterized artery. In this case, the fluid in the tubing and the bubble act in analogy to a mechanical mass and spring resonant system. Potential energy stored as compression of the bubble is exchanged with kinetic energy of the fluid moving in the tubing. In a similar way, if the tubing itself or the transducer has a significant change in volume associated with a change in pressure, the system is said to have an excessively high compliance. The potential energy associated with compliance of tubing or transducer causes resonant behavior of the system by the same mechanism as the potential energy stored in an air bubble.

In order to calibrate such direct pressure measurement devices and to instruct personnel in their proper care and operation, blood pressure wave simulators are used. Such simulators commonly employ a pressure generator including an electromagnetic coil. The coil suspension is stiff so that the compliance of the generator is within an order of magnitude of the tubing compliance. Thus the pressure in the generator is responsive to the fluid displacement in the tubing and the generated pressure wave varies as a function of the compliance of that tubing. These stiff suspension simulators are often modified by placing a large air bubble in the otherwise non-compliant fluid chamber at the diaphragm. In one case the bubble is 10 cc; while the introduction of an air bubble tends toward solving the compliance problem, it introduces two other problems. First, substantial displacement of the stiff coil suspension is required to compress the bubble sufficiently to develop the required pressure, and because the spring constant is high the net force transmitted to the fluid is small compared to the force generated by the current in the coil; and second, because the spring force is high compared with the force transmitted to the fluid, the developed force is very dependent on the volume of the compliant air bubble in the chamber. Therefore the bubble's size must be controlled, which introduces another step in the procedure of setting up the simulator.

SUMMARY OF INVENTION

It is therefore an object of this invention to provide an improved pressure simulator which more faithfully reproduces a particular pressure wave.

It is a further object of this invention to provide such a simulator which is highly accurate and reliable for testing accuracy and performance of transducers, monitors, catheters, tubes, valves, and other electrical and hydraulic parts common to the system and direct pressure measuring devices.

It is a further object of this invention to provide such a simulator which is easy to use for teaching proper techniques for operating and maintaining direct pressure measuring devices.

It is a further object of this invention to provide an improved high compliance, high efficiency pressure generator adapted for use in such a simulator.

It is a further object of this invention to provide such a pressure generator whose compliance is much greater than that of the remainder of the equipment.

It is a further object of this invention to provide such a pressure generator in which the generated pressure follows linearly the excitation current.

It is a further object of this invention to provide such a pressure generator in which the pressure in the generator chamber is relatively independent of volume of the chamber in the unenergized condition.

It is a further object of this invention to provide such a pressure generator in which the sealing diaphragm is both flexible and inelastic.

The invention results from the realization that an improved, highly accurate pressure simulator can be achieved by using a pressure generator whose compliance is much greater than that of the associated tubes, valves, and other fluid-containing portions of the equipment and that a high compliance generator can be made using a low mass, high compliance coil and piston and a flexible but inelastic sealing diaphragm.

The invention features a variable volume pressure generator for a pressure wave generator which includes a drive magnet and a low mass, drive coil which is energized by an electrical analog of a pressure wave to be simulated and is driven by interaction with a magnet. A low mass, high compliance coil suspension supports the coil relative to the magnet, and a piston is interconnected and driven with the drive coil. There is a pressure chamber with an opening for receiving the piston, and there is a flexible, inelastic diaphragm sealingly engaged with the piston and with the chamber. Passage means extend from the chamber for external connection.

Preferably, the diaphragm is a rolling seal diaphragm and the passage means may include two conduits for use with a pressure generator in a pressure simulator.

The pressure simulator includes an electrical waveform generator and a pressure generator responsive to the electrical waveform generator to produce a pressure wave. The pressure simulator is used in conjunction with a pressure measuring device which includes a pressure monitoring unit, a test pressure transducer with monitoring tubes, and a reference pressure transducer. Both transducers are connected to the inputs of the monitoring unit. The passage means may include a first passage extending from the chamber for connection with the reference pressure transducer mounted very close to the chamber, and a second passage extending from the chamber for connection with the test pressure transducer through the monitoring tubing, which is normally used for connection with a catheter attached to the patient.

In this manner, the pressure wave generated by the pressure generator is sensed as it appears at the chamber by the reference pressure transducer and as it appears at the other end of the monitoring tubing by the test pressure transducer. The electrical outputs of these two transducers are then submitted to the pressure monitor where the two readings can be compared to determine the accuracy of the pressure measuring device both in its electrical components such as the transducers and the pressure monitor, and its hydraulic components such as the monitoring tubing.

DISCLOSURE OF PREFERRED EMBODIMENT

Other objects, features and advantages will occur from the following description of a preferred embodiment and the accompanying drawings, in which.

The invention may be accomplished with a pressure generator formed of a magnet and an electromagnetic coil, which is driven by interaction of the magnetic field generated by the flow of current in the coil and the magnetic field of the magnet. The coil is of low mass and supports a low mass piston. The coil and piston are supported relative to the magnet by a low mass, high compliance suspension. The piston is aligned and received in a chamber and is movably, sealingly attached to the chamber by a flexible but inelastic diaphragm. The chamber may be mounted on a mounting plate and a support frame may be used to attach the magnet to the mounting plate. The chamber has one or more passages for external connection. The magnet, coil, suspension system and support frame may be implemented by a conventional audio speaker such as an Oaktron Industries C 5 HU2. This speaker in conjunction with a 14 mm diameter piston produces a pressure of 0.3 mm Hg per milliampere of drive coil current. Typically, the coil is driven by a power amplifier of conventional design except that current feedback is used so that drive coil current rather than voltage is made proportional to the amplifier input. The power amplifier is driven by an electrical waveform generator such as a Hewlett-Packard type 3310 B function generator or a microprocessor programmed to produce a voltage wave closely approximating a blood pressure wave. The pressure generator in combination with a power amplifier and the electrical waveform generator comprise a pressure simulator system which may be used in conjunction with a pressure monitoring device which also includes a reference and a test pressure transducer, each of which may be a type P23 iD manufactured by Statham Instruments. The test pressure transducer typically has attached to it all the hydraulic parts that are used in normal operation, for example tubes, catheters, valves, and the like. Each of the transducers has its output connected to a pressure monitor unit such as a 78205 manufactured by Hewlett Packard.

Although the description of the preferred embodiment shows a chamber with two outlets which interconnect with two transducers, this is not a necessary limitation of the invention. For example, when a calibration or comparison is not required, the chamber need have only one external connection and only one transducer would be used. Further, although the apparatus described herein involves human blood pressure readings, the pressure generator of this invention may be used to re-create any pressure wave whose analog is supplied by the electrical waveform generator.

Figure 1:
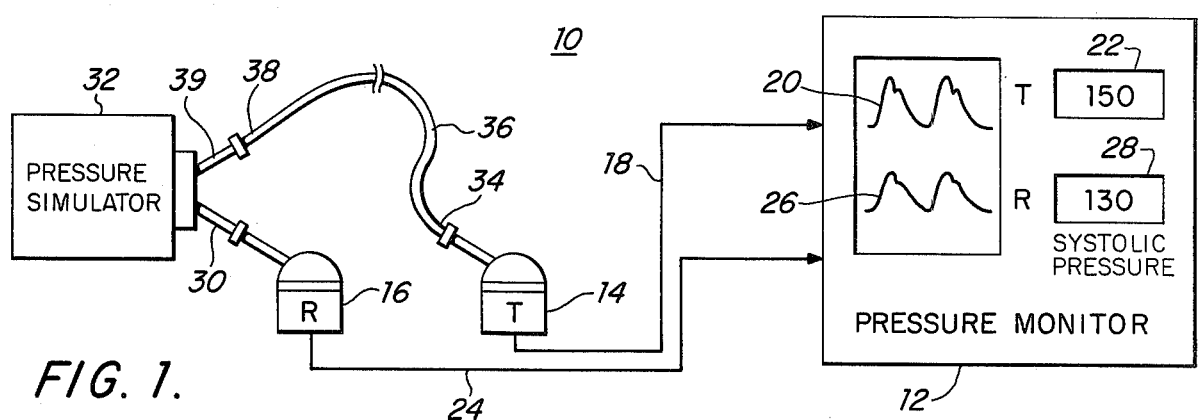
FIG. 1 is a schematic block diagram of a pressure generating and measuring system including a pressure simulator with a pressure generator according to this invention.

There is shown in FIG. 1 a pressure measuring device 10 including a pressure monitoring unit 12, test pressure transducer 14, and reference pressure transducer 16. The pressure variations sensed by test pressure transducer 14 are converted to electrical signals and delivered on line 18 to pressure monitor 12, where the actual wave form 20 may be displayed and the peak value may be determined and displayed in digital readout 22. Similarly, the output of reference pressure transducer 16 is delivered on line 24 and the wave form may be displayed as at 26 with the peak value indicated at digital readout 28. If the pressure being monitored is human blood pressure, readouts 22 and 28 may be labelled with the legend "systolic pressure", for example. Reference pressure transducer 16 is connected directly to one outlet 30 of pressure simulator 32 pressure transducer 14, however, is connected to one end 34 of monitoring tubing 36, whose other end 38 is connected to the other outlet 39 of pressure simulator system 32.

Thus, in operation, with pressure simulator 32 generating a pressure wave which simulates human blood pressure, the pressure developed in system 32 is directly sensed by reference transducer 16 and displayed as at 26, 28, whereas that same pressure wave, after passing through monitoring tubing 36, is sensed by the test transducer 14 with the result displayed as at 20 and 22. In this way clinical personnel can become familiar with the use and operation of the pressure monitoring device and note the difference between the real blood pressure indicated at 26, 28, and the blood pressure indications 20 and 22 which differ because of the intervening tubing 36.

It should be understood that the intervening equipment may and usually does include more complex hydraulic apparatus than monitoring tubing 36, e.g. catheters, needles, and valves. After this calibration has been done, end 38 of monitoring tube 36 can be disconnected from system 32 and lead 24 can be disconnected from the pressure monitor 12. End 38 of tubing 36 is then connected to a needle which is inserted in the arm of a patient, and the patient's blood pressure, distorted by monitoring tubing 36, will be indicated as at 20 and 22, but now with a known determinable factor which can be applied to obtain a correct blood pressure reading; preferably monitoring tubing 36 will include whatever catheters, valves, and other equipment in the calibrating mode as actually used when it is operational and used in connection with patients.

Figure 2:
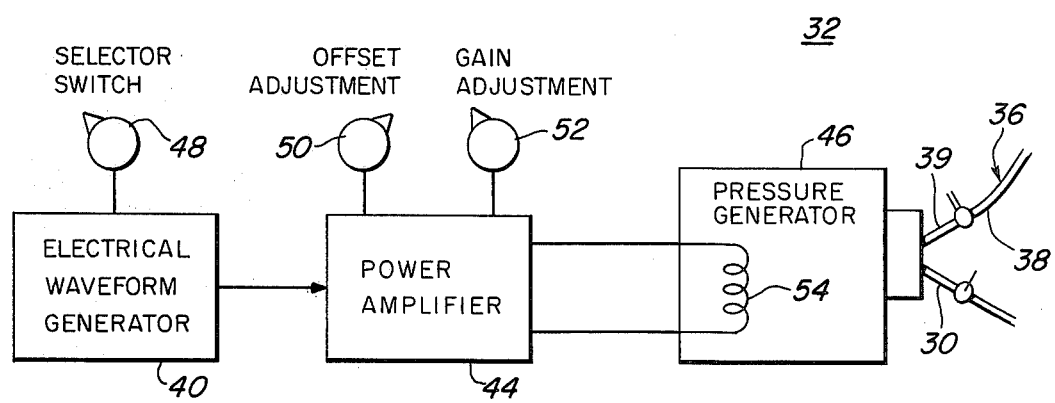
FIG. 2 is a more detailed block diagram of a pressure simulator according to this invention.

Pressure simulator 32, FIG. 2, includes an electrical waveform generator 40, typically a power amplifier 44, and a pressure generator 46. Electrical waveform generator 40 may include a waveform selector switch 48 for selecting any one of a number of predetermined blood pressure waveforms.

Electrical wave form generator 40 may be any conventional wave form generator or a digital processor which outputs digital words from memory which are equivalent to each pressure value in the pressure wave. Power amplifier 44 is a conventional power amplifier with offset 50 and gain 52 adjustments. The output of power amplifier 44 is delivered to coil 54 in pressure generator 46.

Figure 3:
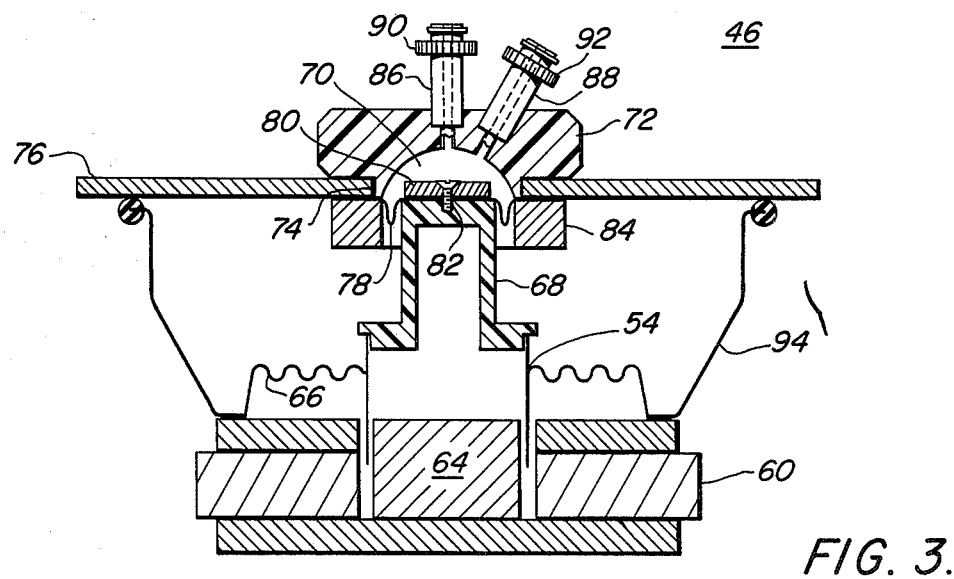
FIG. 3 is a more detailed schematic view of a pressure generator according to this invention.

Pressure generator 46, FIG. 3, includes a drive magnet 60 and a low mass electromagnetic coil 54 which is energized by electrical wave form generator 40 through power amplifier 44, with the electrical analog of the pressure wave to be simulated. The interaction of the field generated by the current in coil 54 and magnets 60 causes coil 54 to move up and down about cylindrical core 64. Coil 54 is supported by a low mass, very high compliance suspension 66 which permits relative motion between magnet 60 and coil 54. Piston 68 is carried by coil 54 and moves with it due to the interaction between coil 54 and magnet 60. Piston 68 is aligned with and received in chamber 70, formed by dome 72 mounted in hole 74 of support plate 76. Piston 68 is sealingly engaged with chamber 70 by means of an inelastic or stiff, but flexible or compliant rolling seal diaphragm 78, which is connected to the top of piston 68 by means of mounting block 80 and screw 82, and to the surrounding edge of dome 72 by means of circumferential pressure ring 84 mounted by screws, not shown, to plate 76. External connection to pressure chamber 70 is made through one or more passages 86, 88, which may contain conventional Luer-Lok connectors 90, 92, for connection to clinical tubes, catheters, and the like. Magnet 60 may be connected to plate 76 by means of a support frame 94.

The extremely low mass and high compliance of suspension 66 and the low mass of coil 54 and piston 68 combine to provide a very high efficiency, high compliance pressure generator in which the pressure generated in chamber 70 is essentially independent of feedback from trapped air bubbles and compliance characteristics of the remainder of the systems, tubes, and hydraulic equipment.

For desired simulation the generated pressure wave follows the electrical energizing waveform. To accomplish this the sealing diaphragm should be stiff or elastic; any movement of the piston is translated directly to the fluid: the diaphragm is not stretched. Stretching of the diaphragm would introduce to the system the force of the diaphragm as it attempts elastically to return to its normal condition. However, in contrast to being stiff, not easily stretchable, the diaphragm is also required to be compliant. Over the normal operating range of the pressure generator the pressure in the chamber, with the coil unenergized, is relatively independent of the volume of the chamber. Pressure in the lines does not stress the diaphragm and cause a back pressure.

Figure 4A:
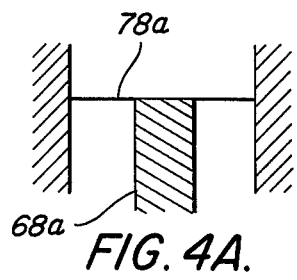
FIGS. 4-7 are schematic diagrams of alternative forms of seals in neutral and deflected positions.
Figure 4B:
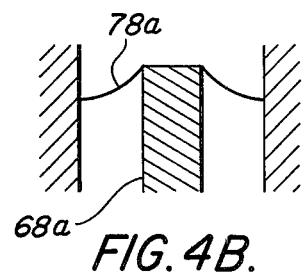
Figure 5A:
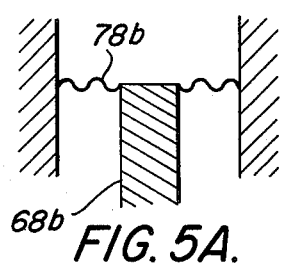
Figure 5B:
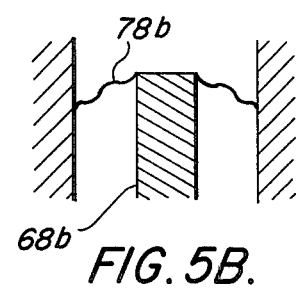
Figure 6A:
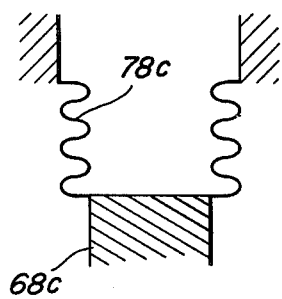
Figure 6B:
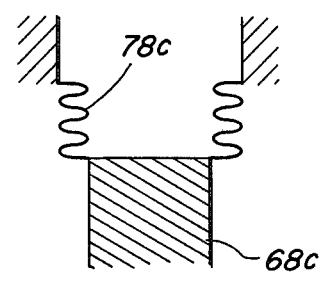
Figure 7A:
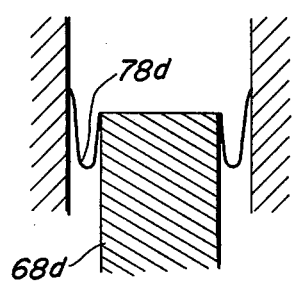
Figure 7B:
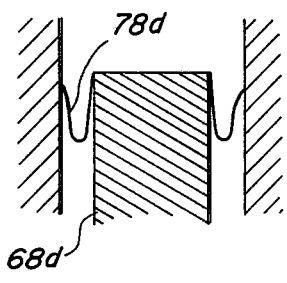

Seals such as illustrated in FIGS. 4 and 5 are not as stiff and compliant as rolling or bellows seals. They tend to stretch and change geometry which results in their spring force entering into the system operation. For example, in FIG. 4A seal 78a when distended, FIG. 4B, by action of piston 68a, stretches and is not fully compliant. Corrugated seal 78b, FIGS. 5A and 5B, reacts similarly, though to a lesser degree. However, bellows seal 78c, FIG. 6A, has considerably better inelasticity and flexibility because of the nature of its accommodation, FIG. 6B, of motion of piston 68c. Rolling seal 78d, FIG. 7A, demonstrates even greater flexibility and inelasticity, FIG. 7B, than the other seals.

Other embodiments will occur to those skilled in the art and are within the following claims:

What is claimed is:

1. A pressure measuring system comprising:
    a high compliance pressure generator for producing a predetermined pressure variation pattern;
    a reference pressure transducer connected directly to said pressure generator for directly sensing the pressure produced therein;
    a test pressure transducer connected through tubing to said pressure generator for sensing the pressure transmitted through said tubing from said pressure generator; and
    a pressure monitor responsive to said test transducer to indicate the pressure sensed through said tubing and responsive to said reference transducer to indicate the pressure sensed directly at said pressure generator for determining the difference in the pressure variation pattern introduced by the tubing.

2. The system of claim 1 in which said pressure generator includes a drive magnet; a low mass, drive coil for energization by an electrical analog of a pressure wave to be simulated and driven by interaction with said magnet; a low mass, high compliance drive coil system for supporting said coil relative to said magnet; a piston interconnected and driven with said drive coil; a pressure chamber having an opening for receiving said piston; an inelastic, flexible diaphragm sealingly engaged with said piston and with said chamber; and passage means extending from said chamber for external connection.

3. The system of claim 2 in which said diaphragm is a rolling seal diaphragm.

* * * * *